(12) United States Patent
Shaw (10) Patent No.: US 12,376,742 B2
(45) Date of Patent: Aug. 5, 2025

(54) VISUAL RESPONSE TRAINING DEVICE AND SYSTEM

(71) Applicant: Thomas J. Shaw, Frisco, TX (US)

(72) Inventor: Thomas J. Shaw, Frisco, TX (US)

( * ) Notice: Subject to any disclaimer, the term of this patent is extended or adjusted under 35 U.S.C. 154(b) by 567 days.

(21) Appl. No.: 17/703,695

(22) Filed: Mar. 24, 2022

(65) Prior Publication Data

US 2023/0301505 A1   Sep. 28, 2023

(51) Int. Cl.
*A61B 3/00* (2006.01)
*A61B 3/028* (2006.01)

(52) U.S. Cl.
CPC .......... *A61B 3/0008* (2013.01); *A61B 3/005* (2013.01); *A61B 3/028* (2013.01)

(58) Field of Classification Search
CPC ....... A61B 3/0008; A61B 3/005; A61B 3/028; A61H 2201/5007; A61H 5/005; A61H 2201/0188; A61H 2201/0192; A61H 2201/5038
See application file for complete search history.

(56) References Cited

U.S. PATENT DOCUMENTS

| | | | | |
|---|---|---|---|---|
| 5,520,543 A | * | 5/1996 | Mitui | A61H 5/00 434/237 |
| 10,806,659 B2 | | 10/2020 | Tolle | |
| 11,980,803 B2 | * | 5/2024 | Koren | A63B 24/0062 |
| 2019/0209419 A1 | * | 7/2019 | Tolle | A61B 3/08 |

FOREIGN PATENT DOCUMENTS

| | | |
|---|---|---|
| CN | 202061038 U | 12/2011 |
| CN | 105476826 A | 4/2016 |
| CN | 108670753 A | 10/2018 |
| CN | 112294611 A | 2/2021 |
| EP | 1499229 B1 | 11/2012 |
| GB | 2571167 | 8/2019 |
| KR | 100305121 B1 | 9/2002 |
| WO | 2021015382 | 1/2021 |

OTHER PUBLICATIONS

Bernell, Eyeport II Vision Training System, https://www.bernell.com/product/JLEPV2/Brock-String-Devices, p. 1/7-7/7.

* cited by examiner

*Primary Examiner* — Mohammed A Hasan
(74) *Attorney, Agent, or Firm* — Scheef & Stone, LLP; Robin L. Barnes; Mike Schofield (57) ABSTRACT

A visual response and training device and system comprising a fixed vision divider panel that is configured to sequentially light a plurality of differently colored LED bulbs each separately visible to only one eye of a user to promote visual tracking in a non-dominant eye. The subject device and system can optionally be configured for testing peripheral vision to sequentially light LED bulbs spread over a range of viewing angles ranging up to about 90 degrees laterally from center in each direction from the respective eyes of a user.

11 Claims, 9 Drawing Sheets

VISUAL RESPONSE TRAINING DEVICE AND SYSTEM

FIELD OF THE INVENTION

This invention relates to an apparatus useful for diagnosing and treating amblyopia, sometimes referred to as "lazy eye," that is often characterized by one weaker eye that wanders inwardly or outwardly instead of tracking the movements of the other, more dominant, eye. The subject apparatus desirably includes a visual response training device and an associated system for using the device to diagnose and treat abnormal or irregular visual responses. In one embodiment, the apparatus is believed to be useful for evaluating, treating and improving visual tracking, depth perception and visual acuity. When configured differently, the subject apparatus is also believed to be useful for evaluating and improving peripheral vision.

BACKGROUND

Amblyopia generally develops before age seven and is a leading cause of visual impairment among children. Patients with untreated amblyopia can experience significant disability or an inability to track moving objects when engaging in daily activities, occupational pursuits or sporting interests such as baseball, basketball, tennis, bowling, hunting, and the like.

Traditional treatment for amblyopia can include eye patches, drops, glasses or contact lenses, and sometimes surgery.

Prior references disclosing some aspects and features of devices, apparatus and treatment methods for various types of visual impairment and performance include, for example, CN108670753A (Vision Training Device—Oct. 19, 2018); EP1499229 (Device and Method for Exercising Eyes—Nov. 7, 2012); CN202061038U (LED linear training instrument for eye vision—Dec. 7, 2011; CN112294611; CN105476826; KR1000305121; WO2021/015382 (Eye Movement Device—Jan. 28, 2021; and GB2571167 (Eye Exercise Device—Aug. 21, 2019)

EYEPORT® II HomeVision Training System manufactured and distributed by Bernell (www.bernell.com/product/JLEPV2/Saccadic_Training; pp. 1/7-7/7) is said to be a visual response recognition and training device for improving the visual response. As disclosed and claimed by Bernell:

"What makes the EYEPORT® II unique is its patented use of alternating red and blue lights . . . . Basically, your eyes react differently to red and blue lights due to a scientific phenomenon called chromatic aberration. The focusing system contracts when it sees red and relaxes looking at blue. By combining eye exercises with specific colored lights, the EYEPORT® II strengthens your vision skills in a revolutionary new way never previously done." [p. 4/7]

Figure 12:
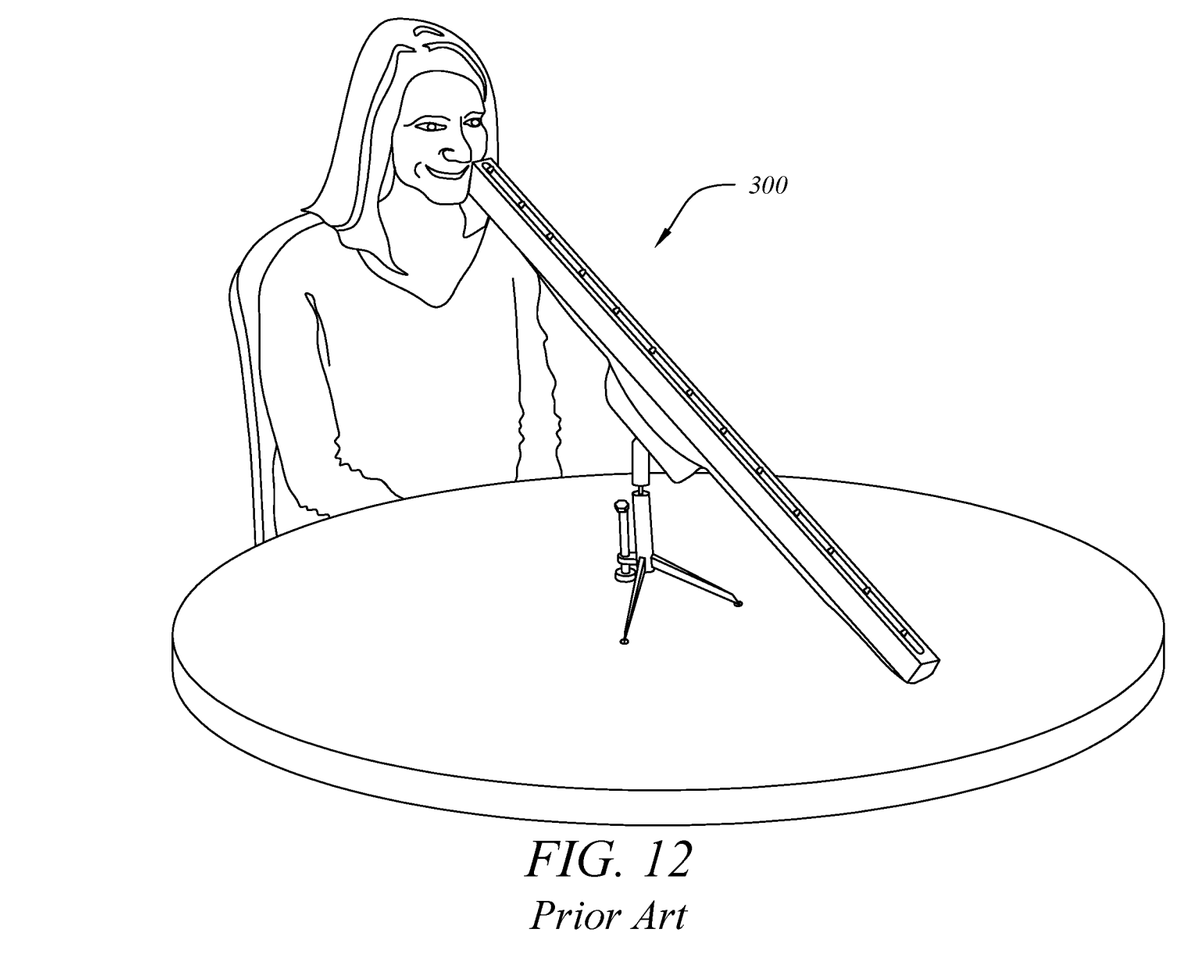
FIG. 12 is a simplified diagrammatic view of the EYE-PORT® II Home Vision Training System prior art device referred to in the Background.

A diagrammatic image identified as "Prior Art" in FIG. 12 of the accompanying drawings, shows pertinent features copied from a photograph on the website www.bernell.com/product on Mar. 7, 2022 appears to show the EYEPORT® II device mentioned above that embodies a single, linear array of LED bulbs, has no vision divider panel that prevents the user from seeing the array with both eyes at the same time, and requires the use of alternate red and blue lights in the single array.

SUMMARY OF THE INVENTION

A visual response training device and associated system are disclosed that comprise a centrally disposed vision divider panel having two parallel, linear arrays of lights, preferably LED bulbs, with one array being located on each side of the vision divider panel to permit viewing of only one array by each eye of a user. Such device can also be used to evaluate peripheral vision by rotating the device left or right relative to the eyes of a user and closing or blocking vision in one eye while continuing to look straight ahead.

In another embodiment of the invention, the two linear arrays of lights are attached to a light bar that is pivotably mounted relative to the vision divider panel so that the light bar can be selectively positioned parallel to the vision divider panel for use in evaluating and treating visual tracking in a non-dominant eye to improve visual acuity, focus and recognition response time of a user. Alternatively, the light bar can be selectively positioned in perpendicular relation to the vision divider panel for use in evaluating and treating peripheral vision in one or both eyes of a user. In this embodiment, the midpoint of the light bar can be pivotably mounted relative to the vision divider panel or the position of the pivotable mounting can be made adjustable to increase or decrease the viewing angle from the user to the outermost lights on the light bar.

In another embodiment of the invention, a system is disclosed that comprises the visual response training device of the invention in combination with an AC/DC electrical power supply (PS) and a programmable control unit (PCU) with a timer configured to selectively energize and de-energize each of a plurality of LED bulbs in such colors and in a desired sequence, duration and interval that is consistent with implementing a predetermined test protocol intended to diagnose and treat symptoms of a suspected or actual medical condition relating to the visual functionality of a patient with whom the subject system is being used. To facilitate such diagnosis and treatment, the system of the invention can also further comprise any of several ancillary input and recording devices such as a digital camera, microphone, instructional input device (keyboard) for the PCU, timer, visual display and data storage device. The system devices can be operably interconnected by any suitable known and commercially available technology such as, for example, wires or cables, wireless networking such as Wi-Fi or Bluetooth, radio frequency (RF) telecommunications, and such transducers, transformers, transmitters, receivers, and the like, as may be satisfactory for use in and desirable to implement the respective technologies for the stated purposes.

Other advantages and benefits of the subject device and system over the prior art will become evident upon reading the entire disclosure in conjunction with the appended drawings.

BRIEF DESCRIPTION OF THE DRAWINGS

The invention is further described and explained in relation to the following drawings wherein.

DESCRIPTION OF PREFERRED EMBODIMENT

Figure 1:
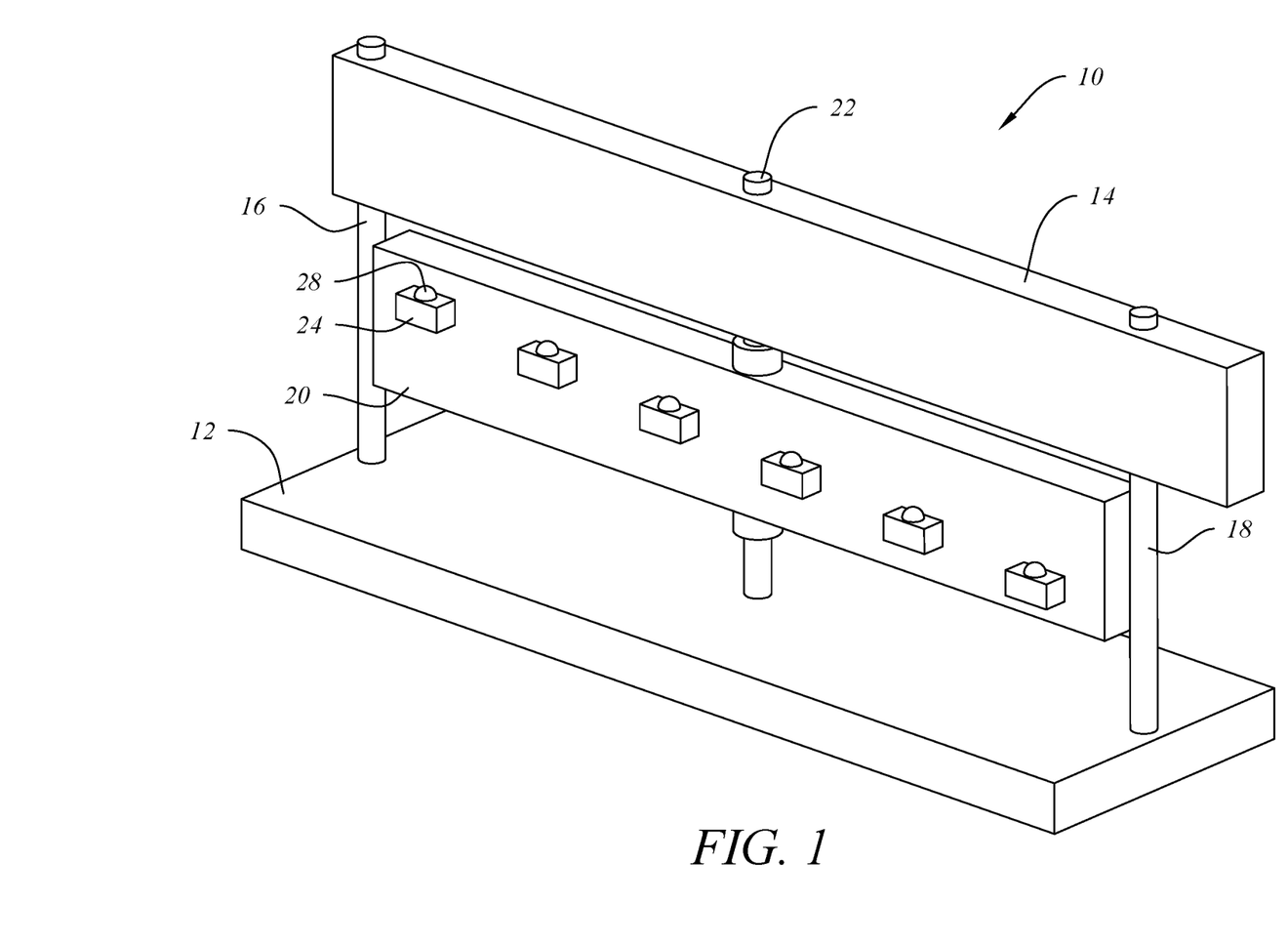
FIG. 1 is a simplified left side perspective view of one embodiment of a visual response training device of the invention.
Figure 2:
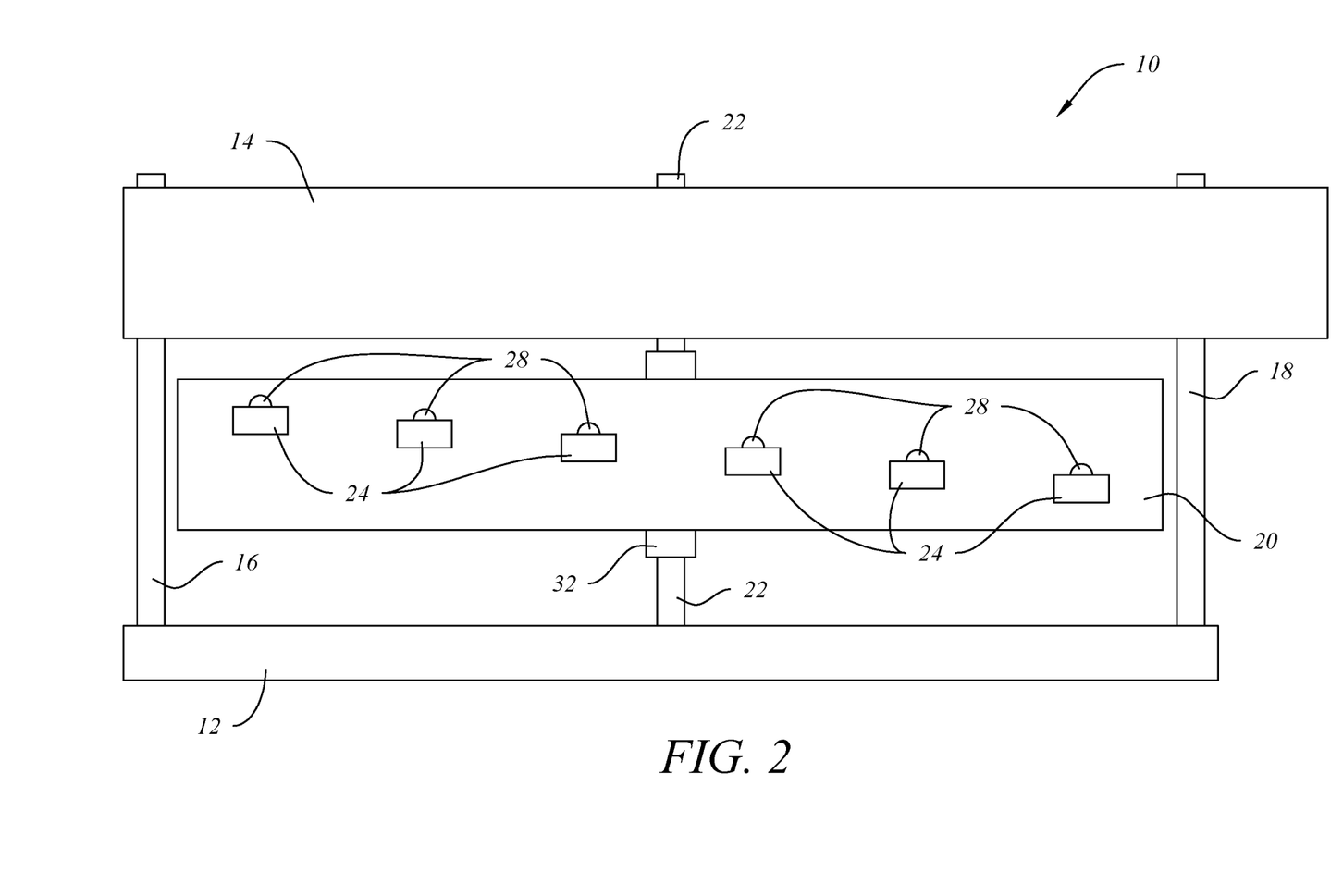
FIG. 2 is a simplified left side elevation view of the embodiment of FIG. 1.
Figure 3:
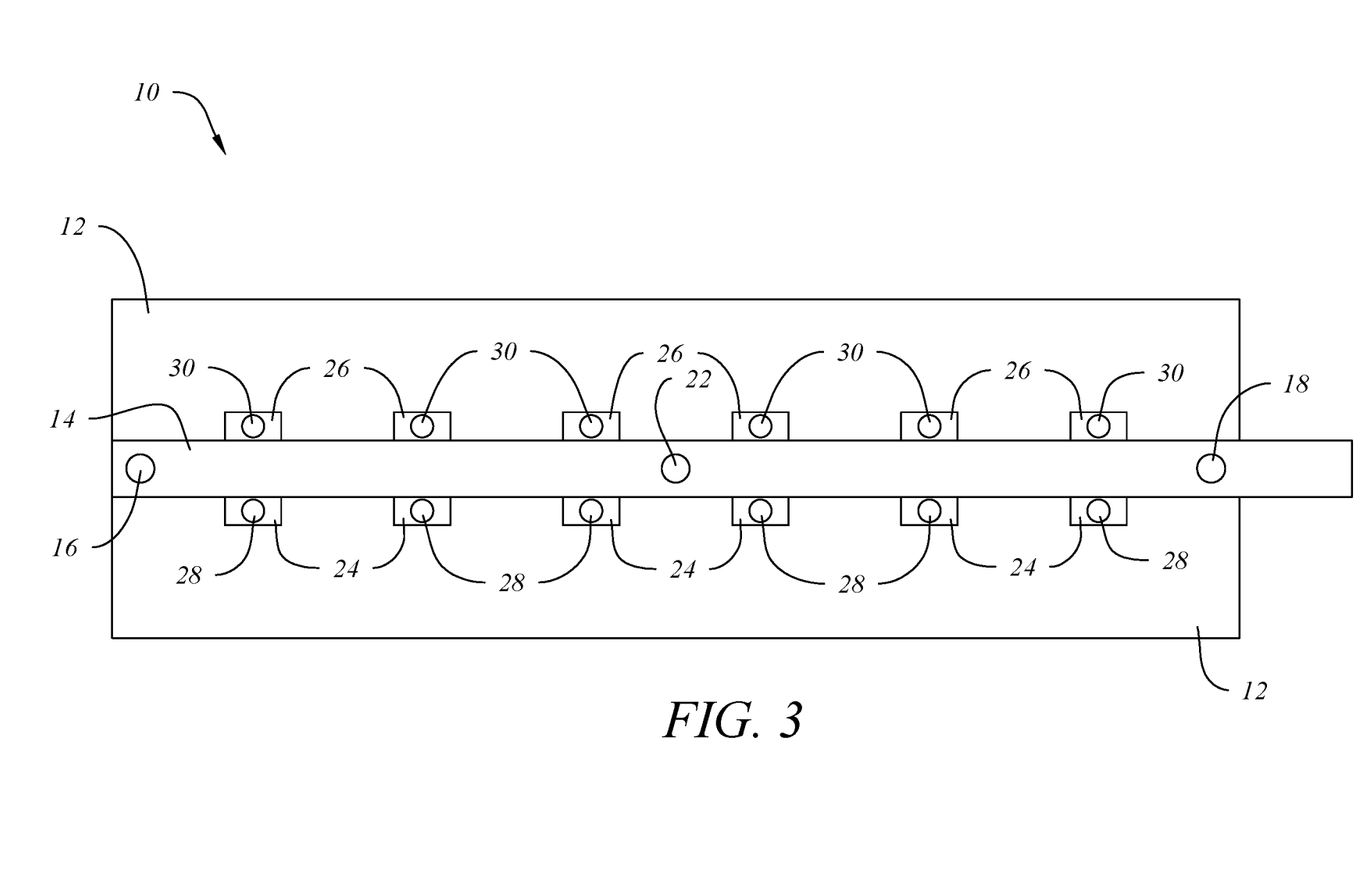
FIG. 3 is a simplified top plan view of the embodiment of FIG. 2.
Figure 4:
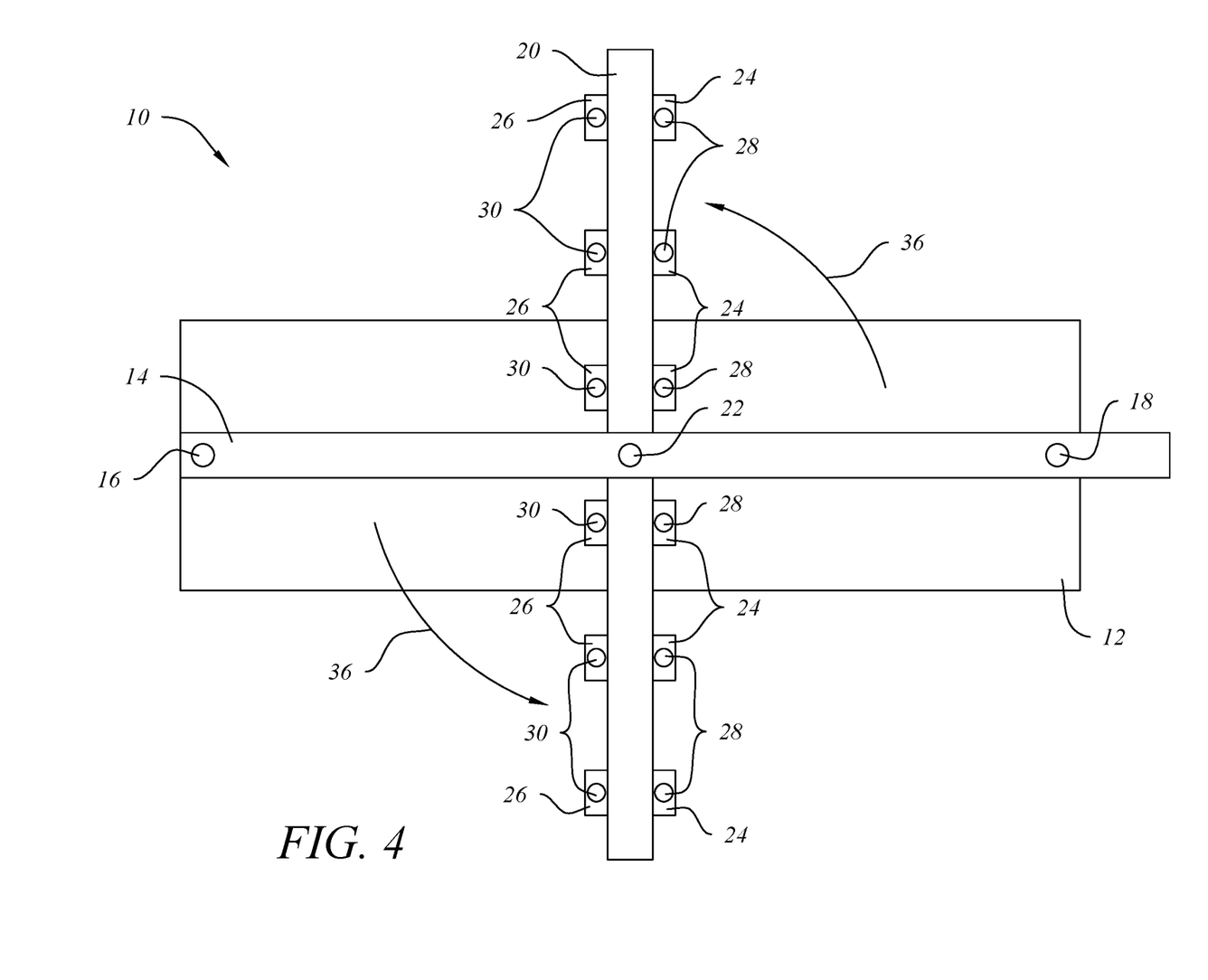
FIG. 4 is a simplified top plan view of another embodiment of the device as in FIG. 3 with the light bar pivoted 90° counterclockwise relative to the vision divider panel as indicated by the arrows shown.

Referring to FIGS. 1-3 of the drawings, visual response training device 10 comprises base 12, vision divider panel 14, support rods 16, 18 and light bar 20 pivotably mounted on shaft 22 between base 12 and vision divider panel 14. Sufficient clearance is desirably provided between light bar 20 and support posts 16, 18 to permit light bar 20 to be selectively pivoted from the position shown in FIGS. 1-3 to the position shown in FIG. 4 when using visual response training device 10 to diagnose or treat a deficiency in the peripheral vision of a user as further described below. Light bar 20 desirably further comprises a plurality of longitudinally spaced-apart mounting blocks 24 disposed on the left side of light bar 20. The length of base 12 and light bar 20, and the number and longitudinal spacing of mounting blocks 24 disposed on the left side of light bar 20 can vary as desired. Alternatively, mounting blocks 24 can be integrated into a single strip attached to the left side of light bar 20. An LED bulb 28 is desirably mounted in each mounting block 24 in a position that provides a direct line of sight between each individual LED bulb 28 and the left eye of a user 34 of the device when light bar 20 is positioned as shown in phantom outline in FIG. 5 of the drawings. Referring to FIGS. 1-5, 7 and 9, it may be observed that the front end of vision divider panel 14 projects longitudinally outward past base 12 in the embodiment shown. This projection desirably enables user 34 shown in phantom outline in FIG. 5 to have a flatter viewing angle relative to the nearest mounting block 24 and LED bulb 28 disposed on the left side of light bar 20.

Referring to FIG. 3, light bar 20 is not visible, being hidden beneath vision divider panel 14. However, it is evident from FIGS. 3, 4 and 6-7 that each mounting block 28 depicted on the left side of light bar 20 is desirably paired with a corresponding, similarly positioned mounting block 26 and LED bulb 30 disposed on the right side of light bar 20.

Figure 7:
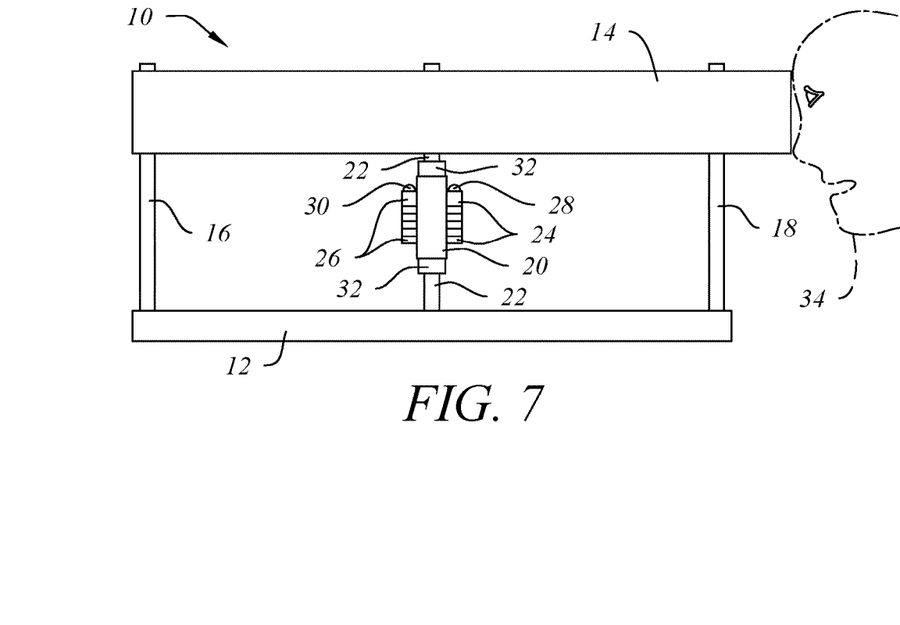
FIG. 7 is a simplified left side elevation view of FIG. 5 with the head of a user shown in phantom outline in a position enabling the user to simultaneously look down the left and right sides of the vision divider panel to see all the LED bulbs in the array mounted on the left side of the light bar as viewed in FIG. 2 when the light bar is rotated 90° counterclockwise relative to the vision divider panel to the position shown in FIGS. 4 and 8.
Figure 8:
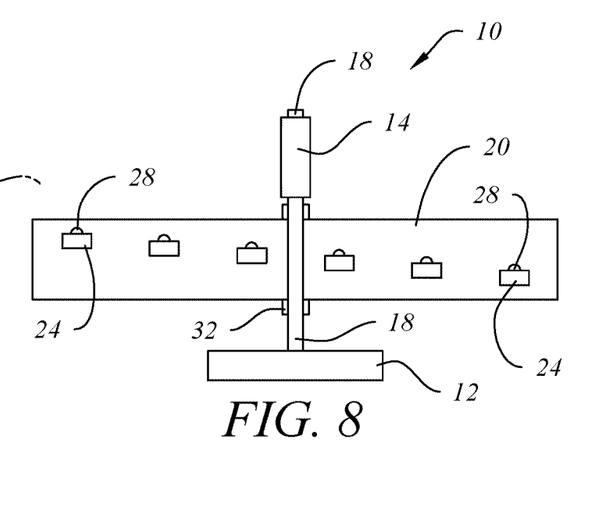
FIG. 8 is the front elevation view of the device as shown in FIG. 4.
Figure 9:
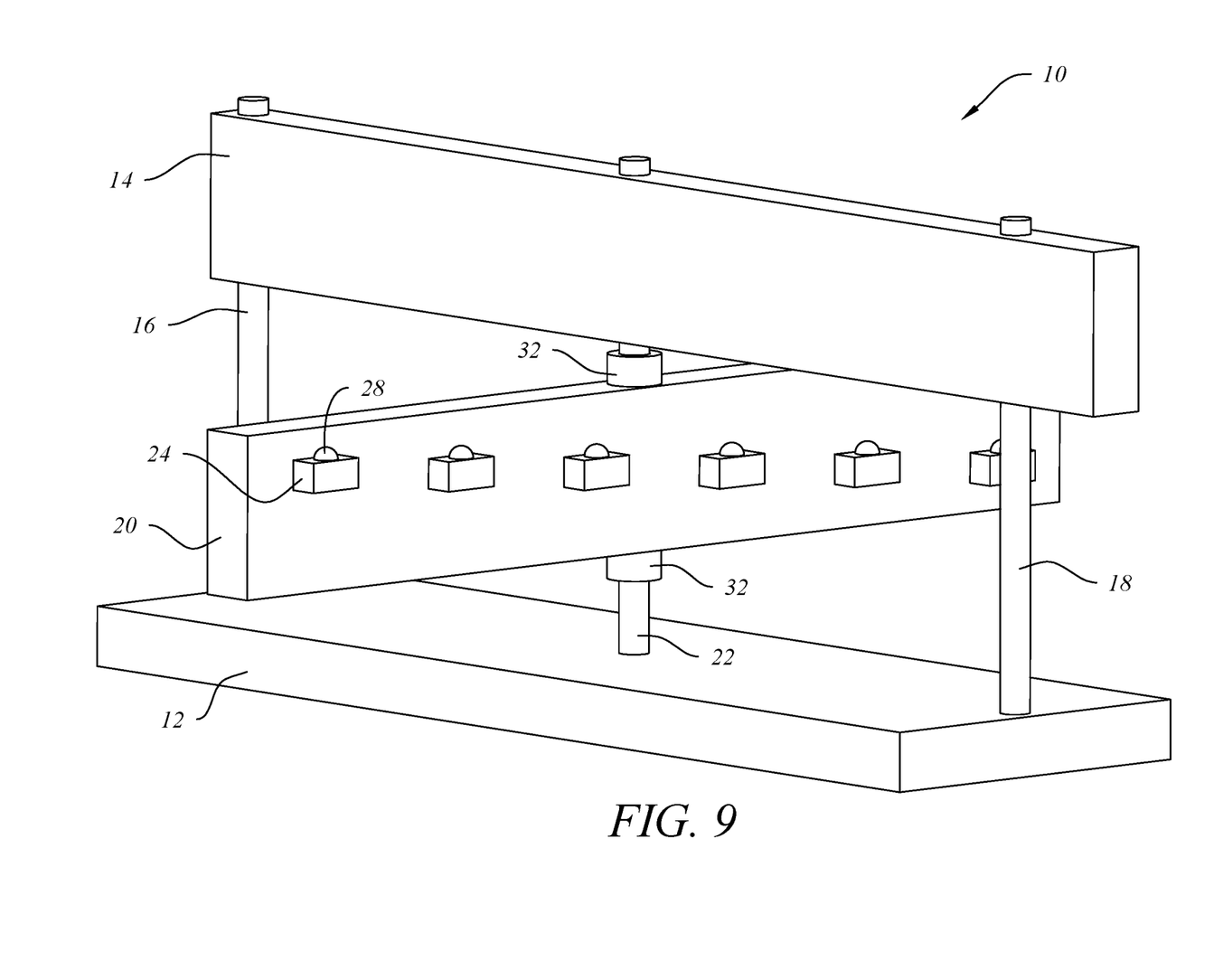
FIG. 9 is a simplified left side perspective view of the subject device when the light bar is rotated counterclockwise from the position shown in FIG. 1 to the position shown in FIG. 4.

Referring to FIGS. 4 and 7-9, another positional embodiment of the invention is seen wherein light bar 20 is selectively pivoted 90° counter-clockwise around shaft 22 relative to vision divider panel 14 as shown by arrows 36, thereby moving from the position shown in FIGS. 1-3 and 5 to facilitate diagnostic testing of the peripheral vision of one or both eyes of a user 34 as shown in phantom outline in FIG. 7. When light bar 20 is positioned as shown in FIGS. 4 and 7-9, only the mounting blocks 24 and LED bulbs 28 disposed on the left side of light bar 20 are visible to the user.

It will become apparent to those skilled in the art upon reading this disclosure in relation to the accompanying drawings that the range of peripheral vision viewing angles for the most distant LED bulb 28 on a light bar 20 of given length can be increased by shortening the longitudinal distance between the user 34 and shaft 22. For this reason, it may be desirable for purposes of increasing the lateral viewing angle during peripheral vision testing to spring-load shaft 22 into connection with base 12 and vision divider panel 14. Doing this will enable rapid repositioning of shaft 22 from the position shown in FIGS. 4, 7 and 9 to alternate, vertically aligned mounting holes provided for that purpose in base 12 and vision divider panel 14 (not shown) that are disposed closer to support rod 18. It will also be apparent upon reading the specification that either of support posts 16, 18 as shown in FIG. 1 can be replaced by one or more functionally equivalent support structures as shown, for example, in FIG. 11 or by another similarly effective device having a cantilevered support structure that can maintain vision divider panel in a desired position and orientation relative to the eyes of a user and to the opposed arrays of light bulbs used to implement various visual testing protocols.

Figure 10:
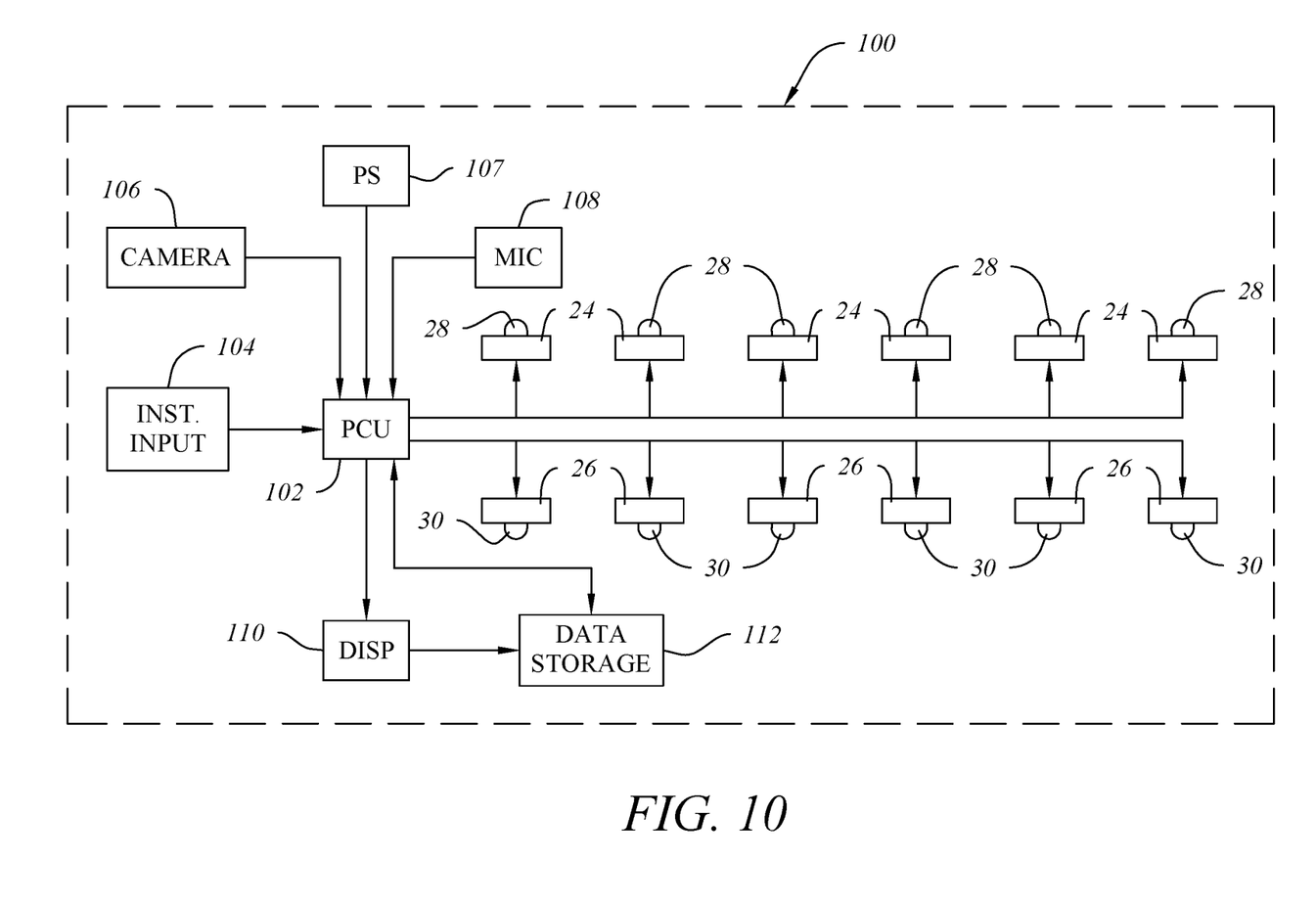
FIG. 10 is a diagrammatic plan view of one embodiment of the system of the invention.

Referring to FIG. 10, system 100 is disclosed that incorporates and operatively combines elements 24, 26, 28 and 30 of vision response training device 10 with ancillary power supply, input, control, display and storage elements that are desirable for use diagnosing and treating medical conditions using the apparatus of the invention. As shown in FIG. 10, system 100 includes: an electrical (AC and/or DC) power supply 107; a digital camera 106 and microphone 108 for capturing and recording visual and audio records of test procedures and patient performance; a programmable controller unit (PCU) 102 operatively coupled to an instructional input device 104 such as a keyboard, hard drive or microphone and configured to selectively energize and de-energize a plurality of locationally identified LED bulbs 28, 30 in a preferred sequential order and predetermined colors at desired intervals for desired duration; and a digital display 110 and data storage device 112 configured to communicate with PCU 102 and tabulate user responses during visual testing and training protocols implemented through use of system 100.

System 100 and vision response and training device 10 are believed to be novel and useful for diagnosing, treating, training, recording and evaluating the visual responses of a user 34 to an array of LED bulbs 28, 30 controllable to present a series of differently positioned and colored stimuli. In one embodiment, the subject invention is primarily useful for improving the visual tracking response in a non-dominant eye. In another embodiment, the subject invention is useful for improving visual acuity, focus and recognition response time with both eyes. In another embodiment, the subject invention is useful for improving the peripheral vision in one or both eyes.

As discussed above, system 100 desirably comprises apparatus such as vision response and training device 10 of the invention, which is configured with a longitudinally extending vision divider panel 14 cooperatively aligned with and centered along a line extending forwardly between the eyes of a user 34. A longitudinally extending light bar 20 is desirably mounted in closely spaced relation beneath vision divider panel 14. Light bar 20 and vision divider panel 14 are desirably supported above a base 12, and all three elements can be made of any suitable, commercially available material selected from wood, plastic, metal or a combination thereof using conventional fasteners and attachment methods. Vision divider panel 14 is desirably positioned so that each eye of observer 34 can only see lights disposed on one side of vision divider panel 14 and light bar 20 even when both eyes are open. Mounted on light bar 20 beneath vision divider panel 14 are a series of longitudinally spaced-apart electric lights, preferably LED bulbs 28, 30, that are laterally equidistant from the barrier and are mounted on a slight upward incline relative to the eye of user 34 to allow a direct line of sight from each bulb disposed on one side of vision divider panel 14 to the user. The LED bulbs 28, 30 are desirably controllable by a programmable control unit (PCU) 102 according to various testing protocols to achieve various visual testing objectives. In a preferred embodiment of the apparatus of the invention, the different testing protocols are pre-programmed into a menu-driven PCU 102 such as a laptop computer or a smart phone.

In another embodiment of the invention, visual response and training device 10 is configured with a vision divider panel 14 as before, but the overall dimension of device 10 and the longitudinal spacing of LED bulbs 28, 30 are selectively adjustable to vary the depth of field. Similarly, light bar 20 can be configured to enable selective adjustment of the lateral distances from vision divider panel 14 to each respective LED bulb 28, 30.

In yet another embodiment of the invention, light bar 20 of the subject device is selectively pivotable around a vertical axis 22 disposed at or near its longitudinal midpoint from a first position that is parallel to vision divider panel 14 to a second position that is perpendicular to the longitudinal axis of vision divider panel 14. When light bar 20 of visual response and training device 10 is pivotably mounted on a vertical shaft 22 disposed at or near the midpoint of vision divider panel 14 and is rotatable through a counterclockwise arc of 90° around the vertical shaft 22 as shown by arrows 36 in FIG. 4, user 34 sees half the LED bulbs 28 extending laterally outward to the left and half the bulbs to the right of vision divider panel 14. When the visual response and training device 10 is configured with light bar 20 rotated 90° relative to vision divider panel 14, device 10 and system 100 can be used to test the peripheral vision of each eye at progressively wider angles from vision divider panel 14. When system 100 of the invention is used in this mode of operation, only the LED bulbs 28 disposed on one side of the light bar are visible to user 34.

EXAMPLE

Figure 5:
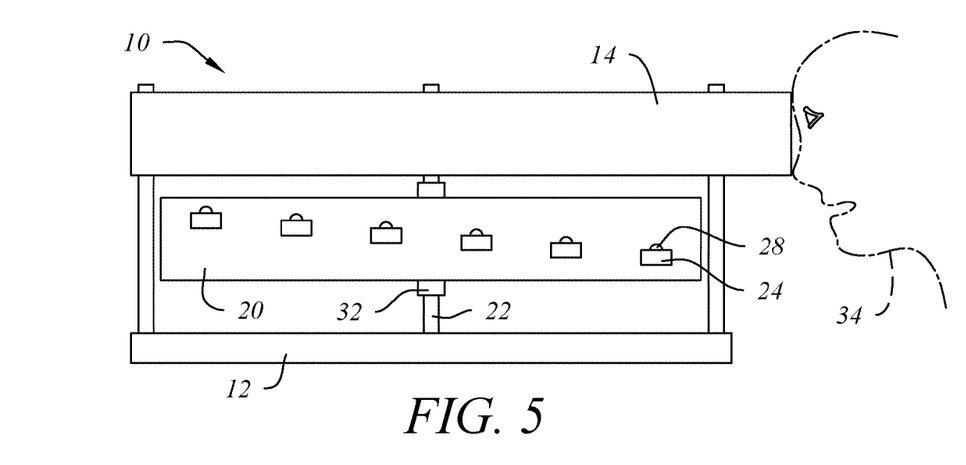
FIG. 5 is the simplified left side elevation view of FIG. 2 with the head of a user shown in phantom outline in a position enabling the user to simultaneously look down the left and right sides of the vision divider panel to see one of the two arrays of LED bulbs mounted on the light bar with each eye.
Figure 6:
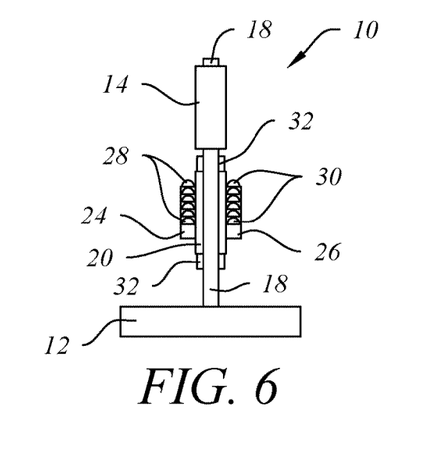
FIG. 6 is a simplified front elevation view of the device of FIG. 2.

An illustrative use of the subject system 100 is described, for example, in relation to a predetermined test protocol that may be implemented after first positioning a user 34 undergoing diagnosis or treatment in a position as depicted in FIG. 5 in relation to visual response training device 10 operatively coupled to other ancillary elements of system 100 as identified and described above.

PCU 102 desirably causes an LED bulb 28 mounted on the left side of light bar 20 pivotably mounted beneath vision divider panel 14 to be energized to display a first color for a half second, followed immediately by energizing a second bulb 30 positioned in a lateral position on the opposite side of the visual divider panel to display a different color for a half second. User 34 undergoing diagnosis or treatment is desirably positioned with one eye looking down each side of the vision divider panel 14 and is asked to identify the colors of the lighted LED bulbs 28, 30 in the sequence in which they are energized.

An operator programs or actively controls the apparatus to cause a pair of LED bulbs 28, 30 disposed on opposite sides of the light bar 20 to light up sequentially. As user 34 call outs the color of each LED bulb 28, 30 disposed on a mounting block 24, 26 as it lights. The positions, sequence, interval, duration and color of successive bulb lightings are all independently programmable and recordable by system 100, together with the responses of user 34, to achieve various purposes related to visual recognition, tracking, acuity, response time, color accuracy, etc. Results from repeated administration of such test protocols are desirably monitored, displayed, recorded, stored and tabulated for each user 34, together with data for testing protocol, light color, distance, response time and correct or incorrect response. If desired, the apparatus of system 100 can include a camera 106 and microphone 108 to facilitate observation, storage and replay of the user's responses during a vision testing protocol.

Figure 11:
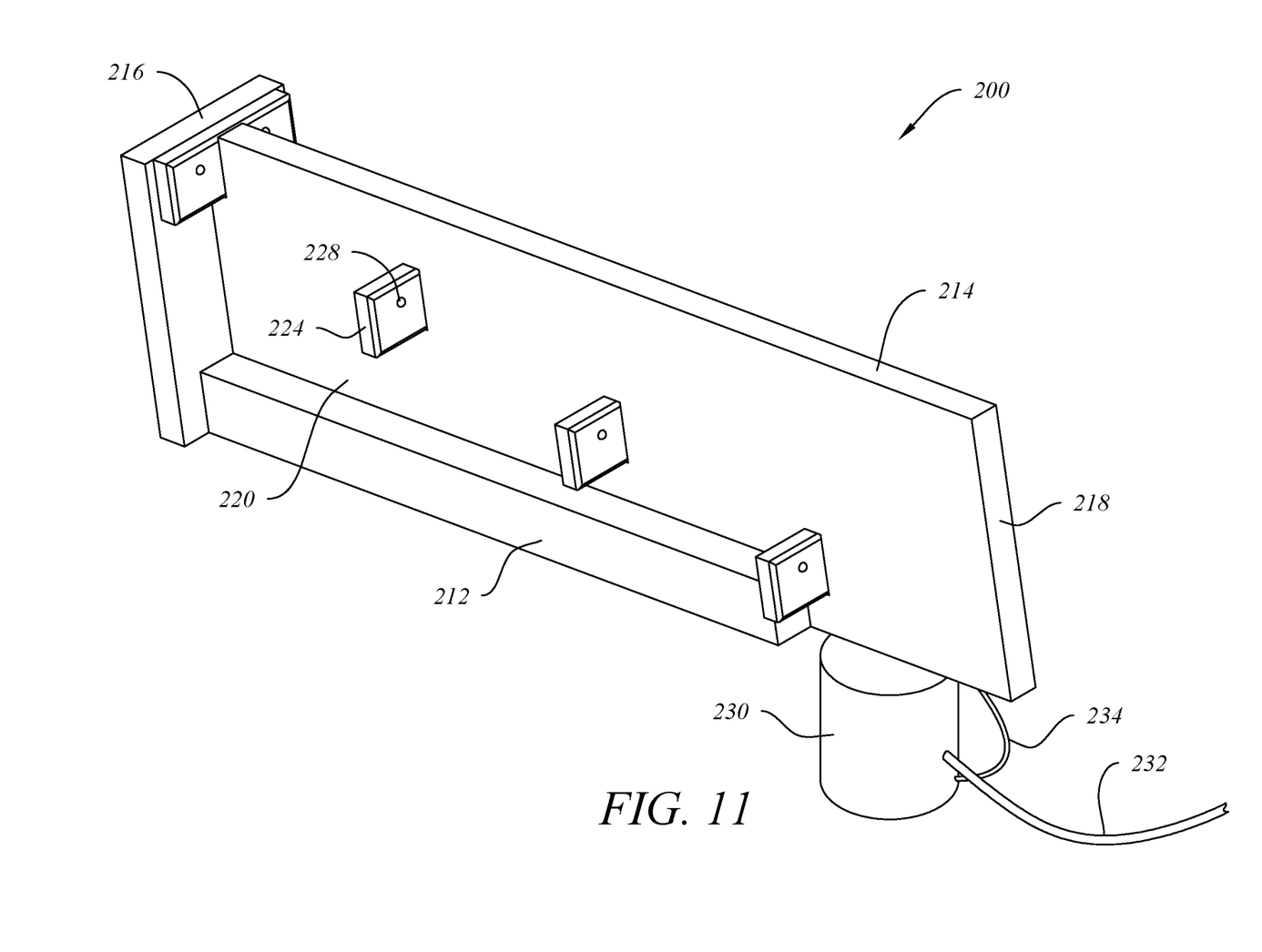
FIG. 11 is a simplified left side perspective view of another embodiment of the subject device in which an inclined array of longitudinally spaced-apart light bulbs is mounted in fixed relation to the vision divider panel instead of a pivotably mounted light bar.

Referring to FIG. 11, a more simplistic system 200 of the invention is disclosed for illustrative purposes that comprises vision divider panel 220 with top and front-end edges 214, 218, respectively supported in the position shown by base 212 and end plate 216. An inclined array of longitudinally spaced-apart mounting blocks 224, each supporting a different light bulb 228 (preferably an LED), is shown attached to one side of vision divider panel 220, with it being understood that a mirror image array is similarly attached to the opposite side of vision divider panel 220 to provide a direct sight line from the other eye of a user looking forwardly along the right side of front-end edge 218. System 200 further comprises digital controller 230 that receives electrical energy from power cord 232 and sequentially energizes each of the light bulbs disposed on each side of vision divider panel 220 to produce a desired color at a desired time for a desired interval according to a predetermined or selectively programmable testing protocol being administered through use of digital controller 230. Still referring to FIG. 11, it should be appreciated that digital controller 230 is positioned so as to provide additional physical support and stability to the front portion of vision divider panel 220 while also elevating front-end edge 218 of vision divider panel 220 relative to the eyes of a user positioned facing front-end edge 218 (similarly to the position of user 34 as shown in FIG. 5).

It will become apparent to those of ordinary skill in the art upon reading this specification in relation to the accompanying drawings that various other modifications and alterations to the disclosed apparatus and methods can also be made, and it is intended that the scope of the invention disclosed herein be limited only by the broadest reasonable interpretation of the appended claims to which the inventor is legally entitled.

What is claimed is:

1. A visual response and training device, comprising:
   a longitudinally extending vision divider panel comprising a first end configured to be positioned proximally between a right eye and a left eye of a user;-and
   a plurality of left lights longitudinally spaced apart and disposed on a left side of the longitudinally extending vision divider panel, each of the plurality of left lights configured to provide a substantially direct sight line to the left eye of the user; and
   a plurality of right lights longitudinally spaced apart and disposed on a right side of the longitudinally extending vision divider panel, each of the plurality of right lights configured to provide a substantially direct sight line to the right eye of the user:
   wherein the longitudinally extending vision divider panel is positioned between the right eve and the left eye of a user such that the plurality of left lights are not visible to the right eye of the user and the plurality of right lights are not visible to the left eye of the user.

2. The visual response and training device of claim 1, wherein the longitudinally extending vision divider panel comprises a first longitudinal side and a second longitudinal side;
   wherein the plurality of left lights are disposed on the first longitudinal side;
   wherein the plurality of right lights are disposed on the second longitudinal side.

3. The visual response and training device of claim 1, further comprising: a light bar;
   wherein the light bar comprises a first longitudinal side and a second longitudinal side;
   wherein the plurality of left lights are disposed on the first longitudinal side;
   wherein the plurality of right lights are disposed on the second longitudinal side; and
   wherein the light bar is selectively movable from a first position parallel to the longitudinally extending vision divider panel to a second position perpendicular to the longitudinally extending vision divider panel.

4. The visual response and training device of claim 3, wherein the plurality of left lights and the plurality of right lights comprises light emitting diodes (LEDs) and each LED is configured to display at least one color of a plurality of colors.

5. The visual response and training device of claim 4, wherein the visual response and training device is configured to selectively activate and deactivate each of the LEDs in any sequence, for any duration, and in any of the at least one color of the plurality of colors.

6. The visual response and training device of claim 5, wherein each LED is selectively activated and deactivated based on an operator input.

7. The visual response and training device of claim 5, wherein each LED is selectively activated and deactivated based on a programmed testing protocol.

8. The visual response and training device of claim 5, further comprising: one or more aligned pairs of LEDs formed by a first LED disposed on the first longitudinal side and a second LED disposed on the second longitudinal side laterally across the light bar from the first LED;
   wherein the first LED is configured to be activated in a first color;
   wherein the second LED is configured to be activated in a second color different from the first color.

9. The visual response and training device of claim 4, wherein the visual response and training device is configured to selectively activate a plurality of pairs of the LEDs, each of the plurality of pairs of the LEDs comprising a first LED disposed on the first longitudinal side and a second LED disposed on the second longitudinal side that are activated in sequence with one of the first LED or the second LED immediately following activation of the other of the first LED or the second LED.

10. The visual response and training device of claim 9, wherein the first LED and the second LED are aligned laterally across the light bar.

11. The visual response and training device of claim 3, further comprising: a base to support the light bar and the longitudinally extending vision divider panel, wherein the light bar is pivotably coupled relative to the base to rotate from the first position to the second position.

* * * * *